United States Patent [19]
Lyster

[11] Patent Number: 5,902,249
[45] Date of Patent: May 11, 1999

[54] METHOD AND APPARATUS FOR DETECTING ARTIFACTS USING COMMON-MODE SIGNALS IN DIFFERENTIAL SIGNAL DETECTORS

[75] Inventor: Thomas D. Lyster, Bothell, Wash.

[73] Assignee: Heartstream, Inc., Seattle, Wash.

[21] Appl. No.: 08/755,273

[22] Filed: Nov. 22, 1996

Related U.S. Application Data

[63] Continuation of application No. 08/399,704, Mar. 3, 1995, abandoned.

[51] Int. Cl.$^6$ .............................. A61B 5/04; A61N 1/39
[52] U.S. Cl. .............................. 600/509; 600/518; 607/5
[58] Field of Search ........................... 600/518, 509

[56] References Cited

U.S. PATENT DOCUMENTS

| | | | |
|---|---|---|---|
| 3,559,193 | 1/1971 | Savaglio et al. | |
| 3,580,243 | 5/1971 | Johnson | 128/696 |
| 3,602,215 | 8/1971 | Parnell | 128/696 |
| 3,868,947 | 3/1975 | Holsinger | 128/639 |
| 3,905,364 | 9/1975 | Cudahy et al. | 128/696 |
| 3,916,878 | 11/1975 | Courtin et al. | |
| 4,112,930 | 9/1978 | Feldman et al. | 128/704 |
| 4,194,511 | 3/1980 | Feldman | 128/696 |
| 4,200,109 | 4/1980 | McMorrow, Jr. | 128/696 |
| 4,243,044 | 1/1981 | Blancke | 128/696 |
| 4,291,699 | 9/1981 | Geddes et al. | 607/6 |
| 4,533,876 | 8/1985 | Haque et al. | 330/253 |
| 4,598,281 | 7/1986 | Maas | 128/696 |
| 4,610,254 | 9/1986 | Morgan et al. | 607/6 |

(List continued on next page.)

FOREIGN PATENT DOCUMENTS

WO 83/01374   4/1983   WIPO .............................. A61B 5/02

OTHER PUBLICATIONS

Klijn, J.A.J. et al., "Movement Artefact Suppressor During ECG Monitoring," *Cardiovascular Research*, (1974) 8:149–152.

Thakor, N.V. et al., "Electrode Studies for the Long-term Ambulatory ECG," *Med. & Biol. Eng. & Comput.*, (1985) 23:116:121.

Grimbergen et al. "A method for measurement of the properties of individual electrode-skin interfaces and the implications of the electrode properties for preamplifier design" *Proceedings of the Annual International Conference of the IEEE Engineering in Medicine& Biology Society* vol. 14 (1992).

*Primary Examiner*—William E. Kamm
*Assistant Examiner*—Carl H. Layno
*Attorney, Agent, or Firm*—Cecily Anne Snyder

[57] ABSTRACT

An apparatus analyzes a composite input signal to determine whether the amount of common mode signal in the composite signal is unacceptably high; thus, precluding an accurate diagnosis of the differential mode signal of interest. Method steps include separating the composite signal input into intermediate signals that are known functions of the differential mode signals of interest and common mode signals (or a suitable combination thereof). In one embodiment, the intermediate signals are cross-correlated to produce a measure of correlation between the intermediate signals. This measure is then compared with a threshold value. If the comparison is favorable, then the data is presumed to be uncorrupted and analysis of the signal representing the differential mode signal continues. Otherwise, the data is presumed to be corrupted and analysis of the signal data is inhibited. In another embodiment, the intermediate signal representing the common mode signal is itself compared against a threshold value without first cross-correlating with the intermediate signal that represents the differential mode signal. If the comparison is favorable, then it may be concluded that the potential for corruption is small and analysis of the intermediate or composite signal is continued.

48 Claims, 8 Drawing Sheets

U.S. PATENT DOCUMENTS

| | | | |
|---|---|---|---|
| 4,619,265 | 10/1986 | Morgan et al. | 607/6 |
| 4,785,812 | 11/1988 | Pihl et al. | 607/8 |
| 4,796,638 | 1/1989 | Sasaki | 128/696 |
| 4,802,486 | 2/1989 | Goodman et al. | 128/633 |
| 4,896,120 | 1/1990 | Kamil | 128/902 |
| 4,917,099 | 4/1990 | Stice | 128/696 |
| 4,919,144 | 4/1990 | Vandehey | 600/518 |
| 4,919,145 | 4/1990 | Marriott | 128/696 |
| 4,993,423 | 2/1991 | Stice | 128/696 |
| 5,002,063 | 3/1991 | Haner | 128/696 |
| 5,020,541 | 6/1991 | Marriott | 128/696 |
| 5,025,808 | 6/1991 | Hafner | 128/696 |
| 5,107,849 | 4/1992 | Bellin et al. | 128/696 |
| 5,184,615 | 2/1993 | Nappholz et al. | 607/4 |
| 5,231,990 | 8/1993 | Gauglitz | 128/697 |
| 5,376,104 | 12/1994 | Sakai et al. | 607/5 |
| 5,392,784 | 2/1995 | Gudaitis | 128/696 |
| 5,427,111 | 6/1995 | Traub et al. | 128/696 |
| 5,474,574 | 12/1995 | Payne et al. | 607/7 |
| 5,503,160 | 4/1996 | Pering et al. | 128/695 R |
| 5,558,098 | 9/1996 | Fain | 607/5 |

METHOD AND APPARATUS FOR DETECTING ARTIFACTS USING COMMON-MODE SIGNALS IN DIFFERENTIAL SIGNAL DETECTORS

This application is a CONTINUATION of application Ser. No. 08/399,704, filed Mar. 03, 1995, now abandoned.

FIELD OF THE INVENTION

The present invention relates in general to a method and an apparatus for detecting artifact signals input into a differential mode signal detector and, in particular, for using common-mode signals, separated from the total input signal, to determine the amount of artifact corruption of the input signal.

BACKGROUND OF THE INVENTION

The presence of common-mode signals in instrumentation systems that are primarily interested in monitoring differential-mode signals is a common phenomenon. Typical examples of a differential-mode signal analyzer include an electrocardiograph ("ECG") monitoring system or a defibrillator system. Electrodes of these system are placed advantageously on the torso of a patient such that the electrical signals generated by the heart induce a differential signal across the electrodes. These differential-mode signals are of interest because they give the diagnostician an accurate indication of the state of the patient's heart (e.g. normal beat pattern versus ventricular fibrillation).

As is well known in the art, common-mode signals (i.e. signals that appear simultaneously upon both electrodes with essentially equal magnitude, frequency, and phase) are superimposed upon the differential-mode signals of interest (i.e. those generated by the heart) and are sometimes converted by the system into differential-mode signals themselves. As discussed in commonly-assigned and co-filed patent application Ser. No. 08/398,377 (entitled "COMMON MODE SIGNAL AND CIRCUIT FAULT DETECTION IN DIFFERENTIAL SIGNAL DETECTORS", filed March 3, 1995 by Leyde et al. and hereby incorporated by reference), this conversion may lead to the ultimate corruption of the differential-mode signals of interest and, in the case of a defibrillator, may lead to a potentially harmful misdiagnosis of the patient's true heart condition.

Because the possibility of misdiagnosis has potentially serious consequences, several attempts have been made to deal with the problem of common-mode conversion. These efforts have, by and large, been concerned with either the elimination or suppression of common-mode signals. By reducing common-mode signals, the contribution of their effects on the composite signal are similarly reduced.

The reduction of common-mode signals has taken several forms. The first common method is capacitance reduction. As is well known in the art, common mode voltages induce common mode currents inversely proportional to the total impedance around the loop between the patient, the system, and the common mode voltage sources. To reduce common mode currents, this impedance is made as large as possible by minimizing the capacitance between the system and its cables to the outside world.

Nevertheless, capacitance minimization has its limitations. Circuits and cabling occupy certain minimum physical areas, and capacitance can only be reduced by increasing the distance from these circuits to outside references. Outside references may be the earth, or objects outside the instrument, or may even be other parts of the same instrument that have different potential references.

For example, many medical instruments maintain "isolated" circuits connected to patients for safety reasons. These circuits maintain a local potential reference not electrically connected to other references in order to reduce accidental electrical injuries. In these cases, reducing the capacitance to such "isolated" circuits means that spacing must be maximized within the instruments between the isolated circuits and other portions of the instrument, the instrument enclosure, or objects in the outside world. However, it is also important to limit the physical size of instrumentation, so that increasing available spacing has practical limitations as a means of limiting common mode currents.

A second major effort to reduce common mode currents is shielding. In this case, shields are equipotential surfaces such as metal enclosures, that are employed to block the entry of electromagnetic fields into instruments and cabling. Such fields may originate, for example, from power lines, radio transmitters, or nearby moving charged objects and may induce common mode currents in circuits they encounter.

However, instrument shielding does not include the patient—a major source of common-mode coupling. The shielding of the instrumentation system thus does nothing to prevent the presentation of large common-mode sources at electrode connections, after which common-to-differential mode conversion proceeds without inhibition. Shielding can, in fact, make matters worse by increasing capacitance between the instrument ground and earth ground, thus facilitating common-mode current flow.

Closely tailored to the inadequacies of shielding, a third common-mode signal reduction method is the use of extra electrodes. In some systems, a third electrode is attached to the patient and connected to the instrument potential reference in an attempt to shunt common-mode currents around the differential electrode leads. Unfortunately, even this third electrode has its own series impedance. Thus, common mode currents will divide between the differential input leads and the third electrode connection. This results in a reduction—but not elimination—of common mode currents in the differential input leads. Also, the addition of a third electrode adds complication to circuitry that minimally requires only two patient electrodes. A fourth method for reducing common-mode signals is filtering. Some common-mode signals, especially at low frequencies (e.g. below 1 Hz) or at power line frequencies, lie outside the normal passband desired for ECG signals (usually between 1–40 Hertz) and thus the composite signal can be improved somewhat by passband filtering. Nevertheless, much of the energy in both common-mode artifacts and ECG signals occupy the same part of the spectrum, which makes attempts to remove all of the common-mode signal futile. Many time-varying fields encountered in patient treatment fall into the normal ECG passband and have time characteristics that are particularly confusing.

As mentioned above, none of these above-described methods for dealing with the presence of common-mode signal completely eliminate the effects of converted common-to-differential mode signal. Thus, the potential for misdiagnosis is still a very real and serious possibility—even after these above suppression techniques have been tried.

Thus, there is a need for a way to effectively deal with the effects of common-mode signal even after suppression of these signals has been attempted. More specifically, there is a need to analyze the composite signal to avoid the possibility of a serious misdiagnosis of patient's condition.

SUMMARY OF THE INVENTION

Other features and advantages of the present invention will be apparent from the following description of the preferred embodiments, and from the claims.

The present invention is a novel method and apparatus for analyzing the composite input signal and determining whether the effects of common mode signal in the composite signal is unacceptably high; thus, precluding an accurate diagnosis of the differential mode signal of interest.

The steps of the presently claimed method are, first, to separate the composite signal input into intermediate signals that are known functions of the differential mode signals of interest and common mode signals (or a suitable combination thereof).

In one embodiment of the present invention, the intermediate signals are cross-correlated to produce a measure of correlation between the intermediate signals. This measure is then compared with a threshold value. If the comparison is favorable, then the data is presumed to be uncorrupted and analysis of the signal representing the differential mode signal (i.e. either the composite signal or the intermediate signal of known function of differential mode signal) continues. Otherwise, the data is presumed to be corrupted and analysis of the signal data is inhibited.

In another embodiment, the intermediate signal representing the common mode signal is itself compared against a threshold value without first cross-correlating with the intermediate signal that represents the differential mode signal. If the comparison is favorable, then it may be concluded that the potential for corruption is small and analysis of the intermediate or composite signal is continued. Otherwise, the potential for corruption is deemed to be too great and analysis of signal data is inhibited. The intermediate data signals are derived from the use of a novel differential amplifier circuit disclosed herein and in the above-incorporated application of Leyde et al. The two intermediate data signals are then digitized by an A/D converter and input into a microprocessor for further processing.

The microprocessor normalizes the digital data and cross-correlates the data according to a cross-correlation function specified herein. The resulting cross-correlation value is, heuristically speaking, a quantified measure of the amount of common mode corruption present in the input signal.

The cross-correlation value is then compared against an empirically obtained threshold value. If the cross-correlation value is less than the threshold value, then the input signal data is presumed to be relatively uncorrupted and evaluation of the input data is continued to determine if the patient is experiencing fibrillation. Otherwise, the input data is presumed to be corrupted and the system takes no action on the data.

One advantage of the present invention is that the remaining common-mode signal that cannot be completely eliminated by prior art techniques is extracted to provide valuable data about the amount of converted common-mode corruption that exists in the input signal. If it is adjudged that the degree of corruption is high, then signal data gathered to date can be discarded. Data evaluation then resumes only when the amount of corruption is below a threshold amount.

Another advantage is that the operator of the system can be appraised of the corruption condition and be advised by the system as to what steps to take to reduce the amount of common-mode signal introduced into the system.

For a full understanding of the present invention, reference should now be made to the following detailed description of the preferred embodiments of the invention and to the accompanying drawings.

DETAILED DESCRIPTION OF THE INVENTION

Figure 1:
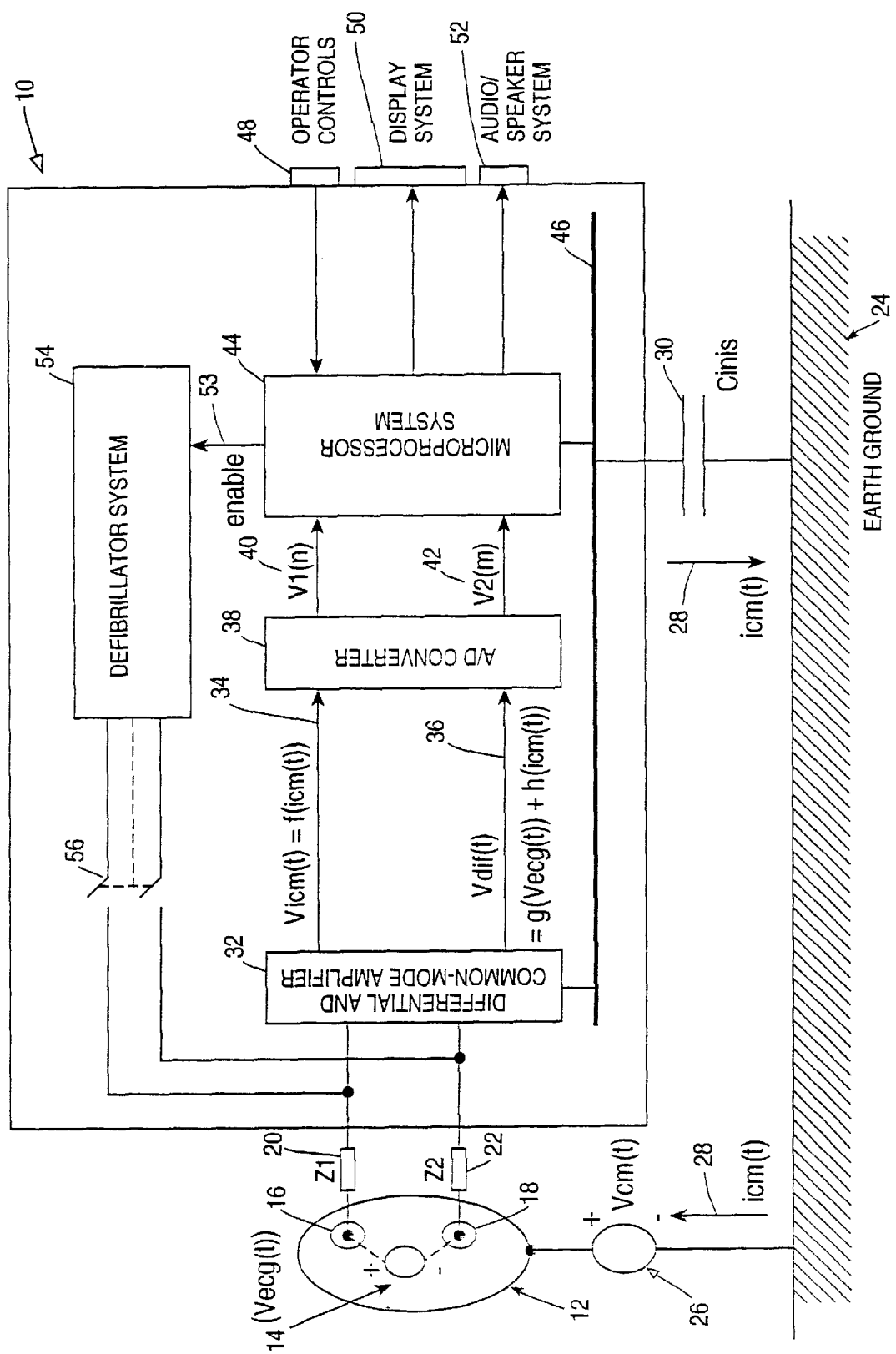
FIG. 1 is a high level block diagram of a signal detector made in accordance with the presently claimed invention.

Referring now to FIG. 1, a high level block diagram of a defibrillator system 10 made in accordance with the presently claimed invention is shown. Defibrillator 10 is connected to a patient 12 by electrodes 16 and 18 advantageously placed proximate to heart 14 which outputs a differential mode signal, $V_{ecg}$. Electrodes 16 and 18 have associated impedances 20 and 22 respectively and are schematically represented by $Z_1$ and $Z_2$.

As is well known in the art, common mode signals may arise through many sources. One such source 26 ("$V_{cm}$") induces a common mode current 28 ("$I_{cm}(t)$") that follows a path in FIG. 1 from earth ground 24, through patient 12 and electrodes 16 and 18, through defibrillator 10, and back to earth ground 24 via a stray capacitance 30 ("$C_{ins}$"). Common mode currents, such as $I_{cm}(t)$, co-exist with (and are superimposed with) differential mode signals generated by the heart.

These superimposed common mode signals are input into defibrillator 10 along with the differential mode signals via electrodes 16 and 18 into differential and common mode amplifier block 32. In a typical amplifier, some amount of common mode signals is converted into differential mode signals and passed along in the output as differential mode signals. In these typical amplifier systems, the converted common mode signals sometimes dominate the output of the amplifier and the potential for misdiagnosis of the differential mode signal of interest exists.

Although the presently claimed amplifier does not entirely eliminate the presence of converted common mode signals from the output, the presently claimed system does separate the input signal into two intermediate signals 34 and 36 that are known functions of the differential mode signals and the common mode signals.

Figure 2:
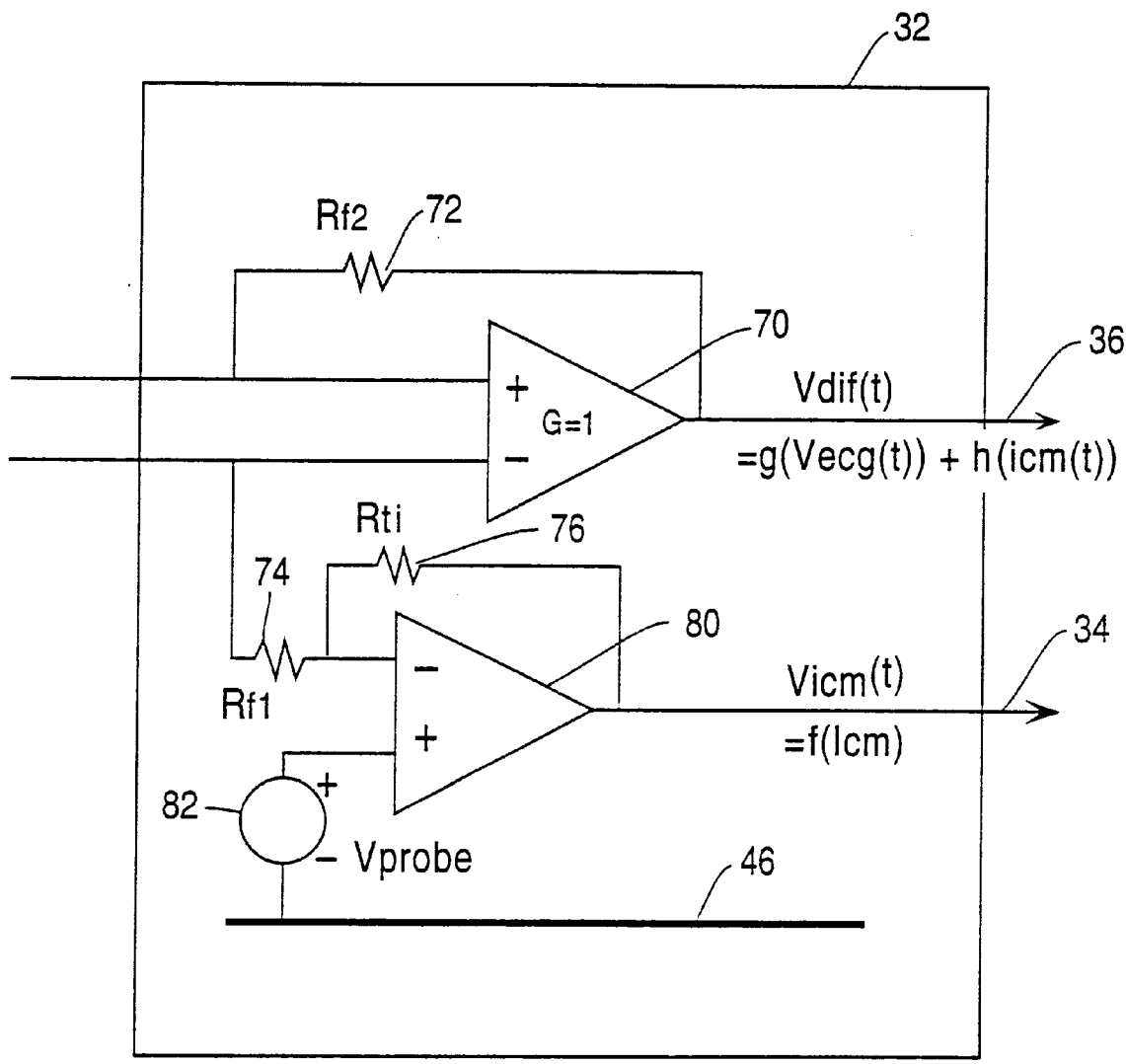
FIG. 2 is a simplified schematic diagram of an input amplifier that separates portions of the differential-mode and common-mode input signals that can be used by subsequent portions of the detector.

A simplified schematic diagram of such a suitable amplifier block 32 that separates the input signal into these two intermediate signals is shown in FIG. 2. Amplifier block 32 comprises instrumentation amplifier 70 having a gain that is substantially unity (i.e. G=1). Amplifier 70 is connected to input electrodes coming from patient 12 that provides the differential and common mode input signals.

Figure 3:
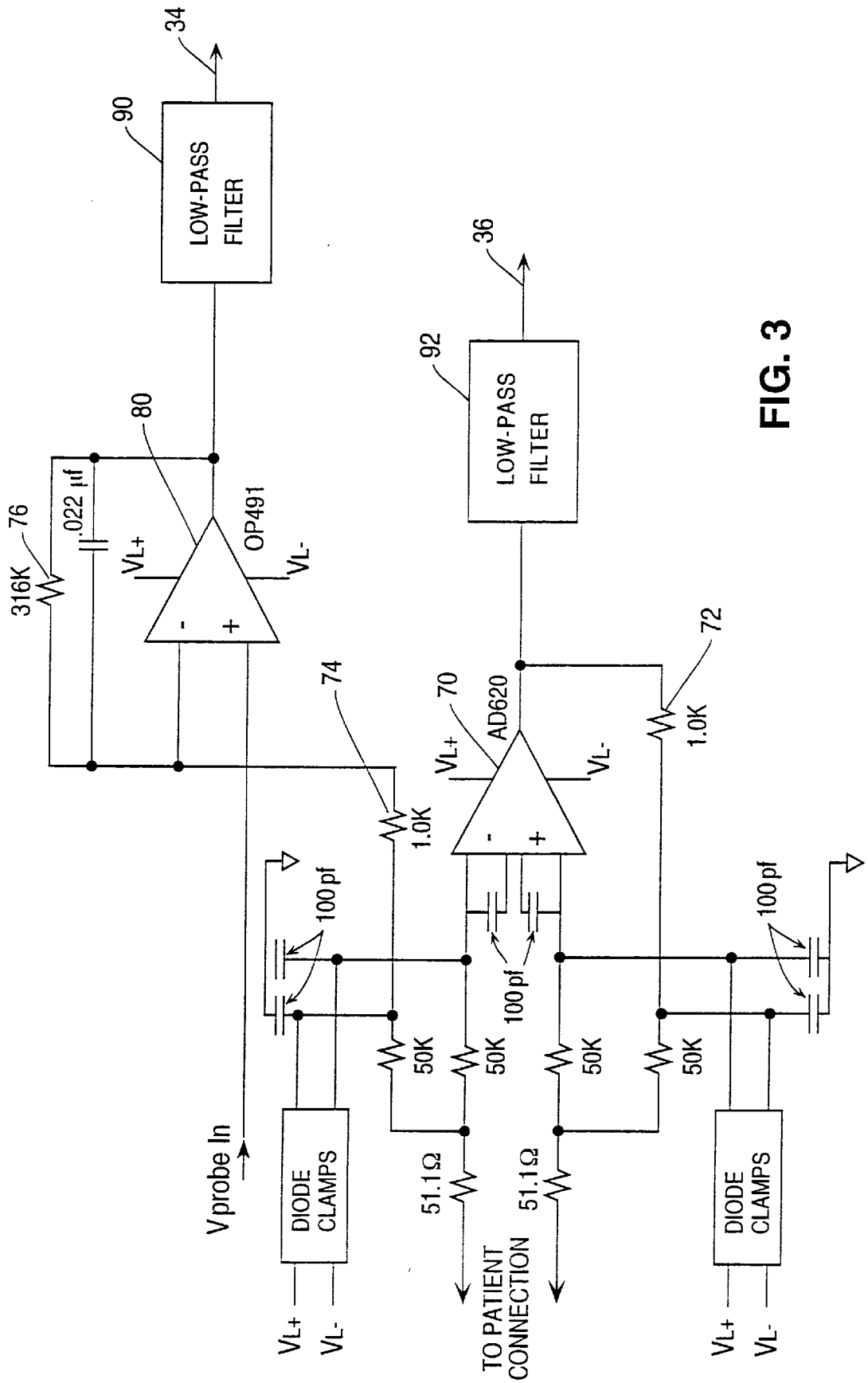
FIG. 3 is a more detailed schematic diagram of the input amplifier as depicted in FIG. 2.

With respect to differential mode input signals, it can be shown (and is shown in the above-incorporated application of Leyde et al.) that input impedance element 72 provides positive feedback to increase the impedance for such differential mode signals. Additionally, it can be shown that intermediate signal 36 of instrumentation amplifier 70, after suitable filtering out $V_{probe}$ (filter 92 as shown in FIG. 3), is a function of both the input differential mode signal, $V_{ecg}$, and the common mode signal, $V_{cm}$. In practice, intermediate signal 36 is usually dominated by the patient's ECG signal, but occasionally, this output becomes corrupted by converted common mode artifacts such that an accurate diagnosis of the differential mode signal component is not possible.

As for the output of operational amplifier 80, it can be shown that, after suitable filtering of $V_{probe}$ (filter 90 as shown in FIG. 3), the voltage at line 34 is approximately $I_{cm}/2 \times R_{ti}$—which is solely a function of the common mode signal.

FIG. 3 is a more detailed electrical schematic diagram of the simplified circuit depicted in FIG. 2 with like components labelled with like numerals. It will be appreciated that while FIG. 3 is a present embodiment of amplifier block 32 having sample component values and component designations, the present invention should not be limited to any particular value or designation of component. Neither should the present invention be particularly limited to the specific circuit arrangement shown in FIG. 3—for the purposes of the present invention, any method for separating the input signals into intermediate signals that are known functions of differential mode signals and common mode signal is sufficient.

Figure 4:
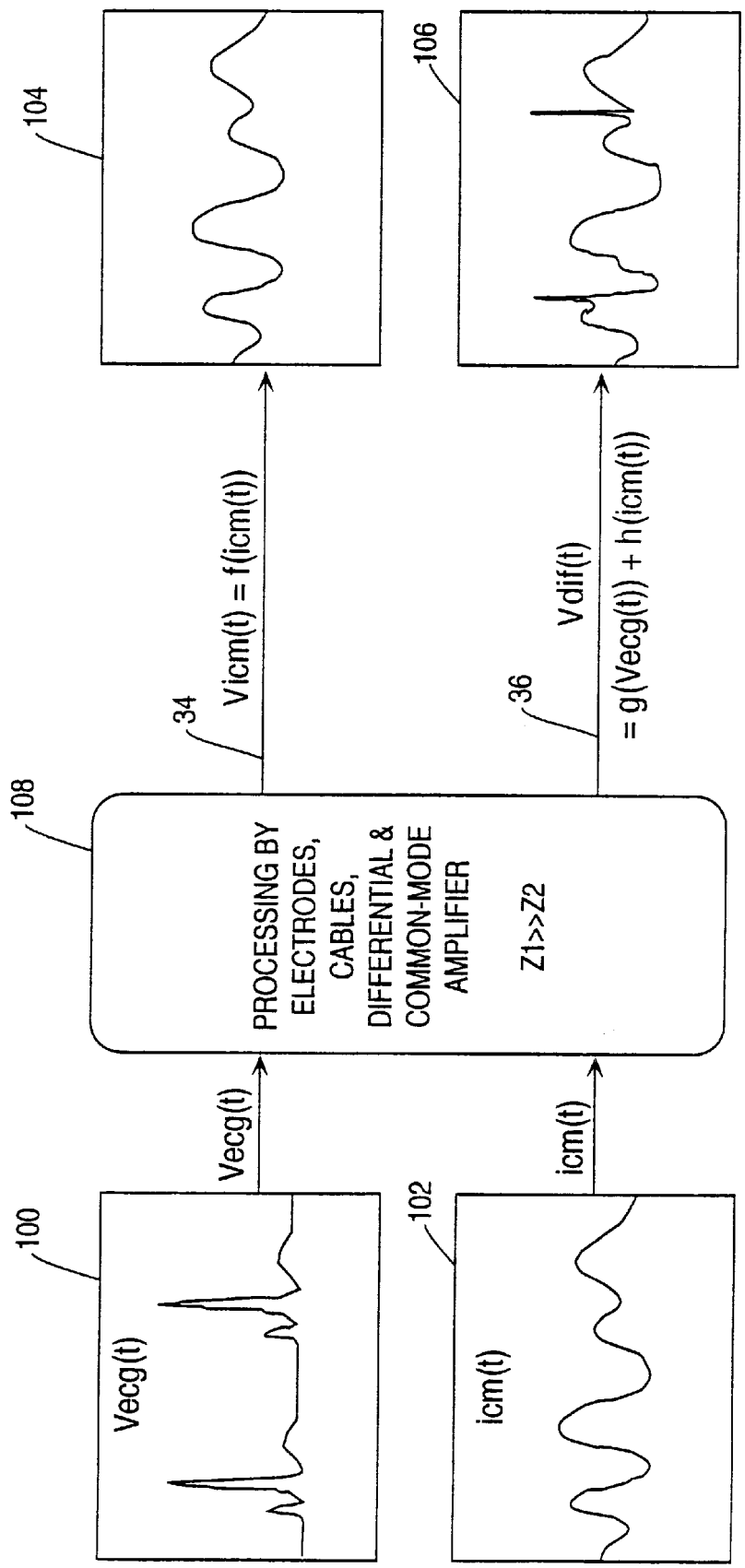
FIG. 4 depicts the processing of input signals by an input amplifier as shown FIGS. 2 or 3 where there is a substantial amount of common-mode signal present and an impedance mismatch on the input leads.
Figure 5:
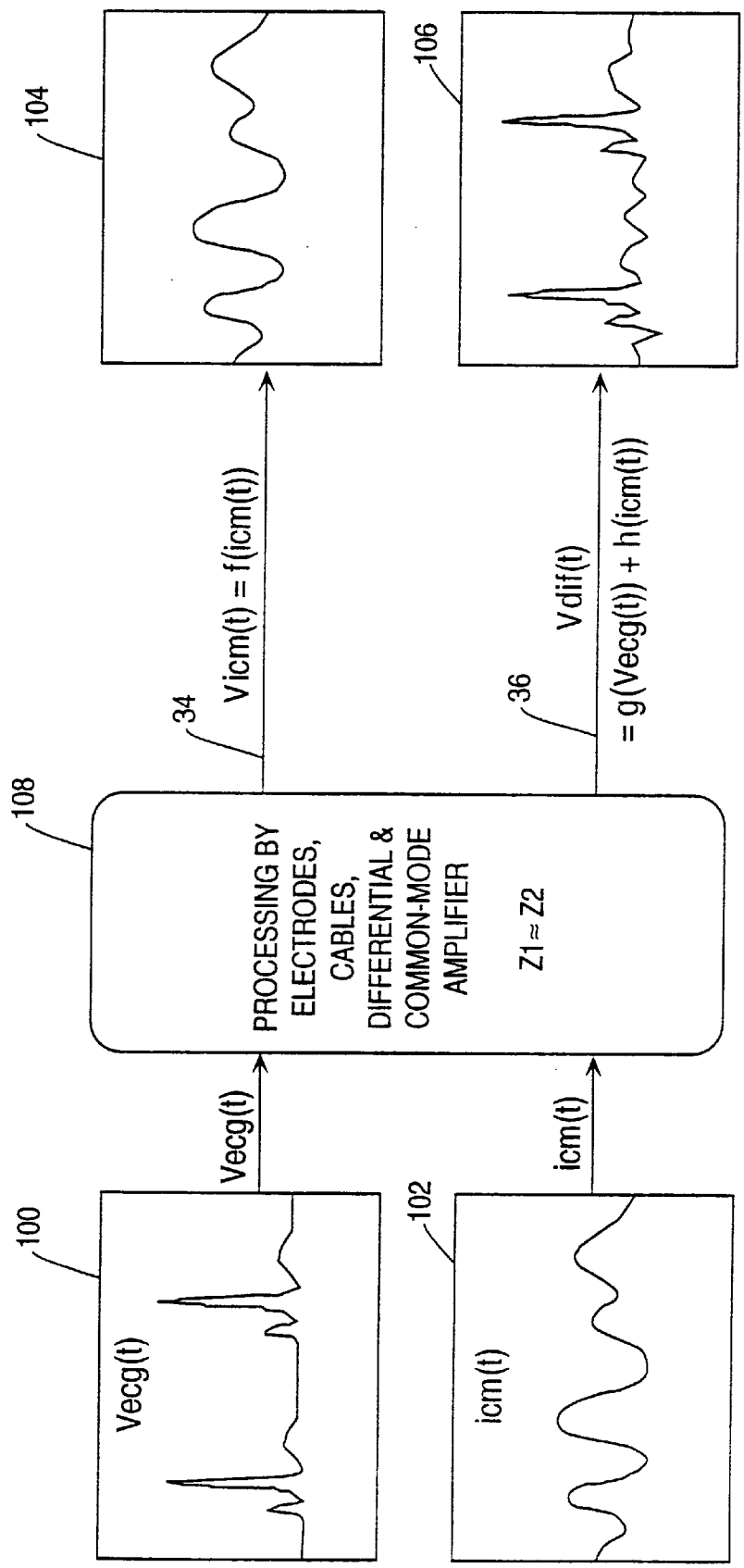
FIG. 5 depicts the processing of input signals where there is the same common-mode signal as in FIG. 4; but where there is no impedance mismatch.
Figure 6:
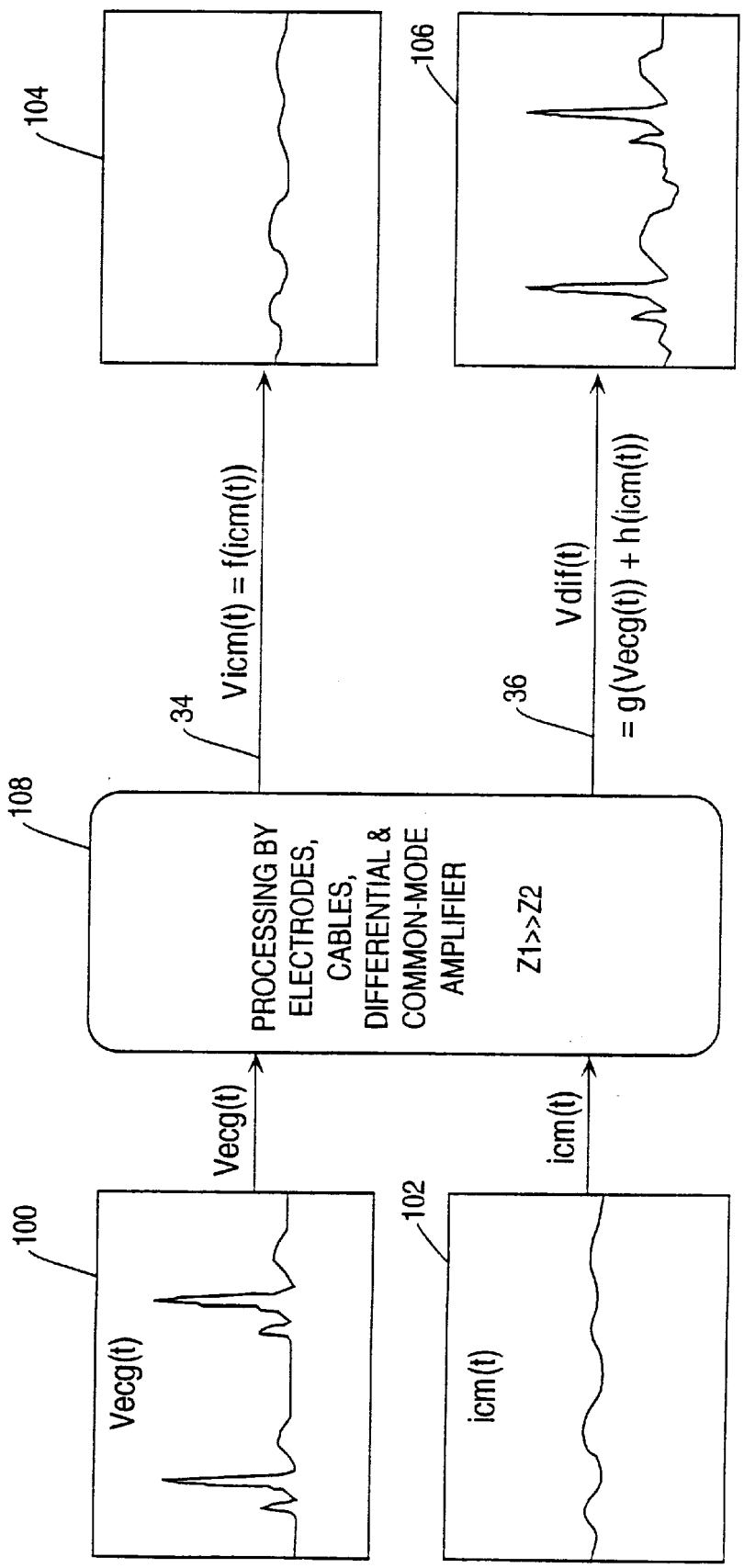
FIG. 6 depicts the processing of input signals where there is comparatively no common-mode input signal but there is an impedance mismatch.

To better illustrate the functioning of the "front-end" portion 108 of the system 10 (where the "front-end" comprises the electrodes, the amplifier block 32 and the cables connecting the electrodes to block 32), FIGS. 4, 5 and 6 depict the functioning of "front-end" 108 in response to sample differential mode input signal 100 and common mode input signal 102. In FIG. 4, it is assumed that there is an impedance mismatch between the two electrodes where $Z_1$ is much greater than $Z_2$. An impedance mismatch might arise for several reasons including the fact that one electrode was improperly placed on the patient's torso. As is well known in the art, such an impedance mismatch increases the amount of converted common mode signal in the output of amplifier block 32.

As can be seen from FIG. 4, the ECG signal 100 is normal; but co-exists with a fairly strong common mode current 102. The front-end 108 separates out the common mode signal 104 on line 34; but, because the amount of converted common mode signal is relatively large, it can be seen that the second intermediate output 106 on line 36 contains a large amount of corruption. In such a case, it is possible that the signal 106 could be misdiagnosed as a heart in a state of fibrillation. However, as will be discussed in greater detail below, the present invention would note that the intermediate output 104 represents a strong common mode signal, that corruption and the potential for misdiagnosis exists, and would prevent any action based upon such a misdiagnosis (e.g. deliver a shock to a patient whose heart rhythm is within normal parameters).

It will be appreciated that it is important to distinguish between the potential for common mode corruption of differential mode signals and the actual presence of corruption. Even though high common mode currents may be present, which under some circumstances give rise to significant signal corruption, such currents may actually present few undesirable effects under more ideal conditions. Simply interrupting analysis of vital ECG information when only potential for corruption is detected may needlessly impede the delivery of therapy to needy patients. It is an important feature of the presently claimed invention to interrupt analysis only when such corruption is detected to be actually present.

FIG. 5 depicts the same front-end circuit 108 faced with the same differential mode and common mode input signals as illustrated in FIG. 4. In this case, however, both electrode impedances are, by good fortune, substantially equal. The opportunity for common-to-differential mode conversion is thereby reduced. Thus, even though common mode signal 104 is undiminished from the example of FIG. 4, its actual effect on the differential signal 106 is not pronounced. On the basis of the small proportion of common mode signal 104 reflected in the differential mode signal 106, the presently claimed system might properly conclude that corruption in the differential mode signal is small; hence intermediated signal 36 is an accurate representation of the differential mode signal emanating from the patient's heart.

FIG. 6 depicts the front-end processing of a normal ECG signal co-existing with a comparatively small common mode signal—where the electrode impedances are again mismatched as in FIG. 4. As can be seen, because the input common mode signal is small initially, the amount of converted common mode signal is also small. Again, as in FIG. 5, the presently claimed system might properly conclude that the degree of differential mode signal corruption is small; and hence intermediate output 36 is an accurate reading of the patient's differential ECG signal.

Returning to FIG. 1, once the two intermediate signals 34 and 36 are produced, they are sampled digitally by A/D converter 38 and digital signals 40 and 42 are produced respectively. It will be appreciated that for the purposes of the present invention, any commercially available A/D converter of sufficient speed and resolution to capture the input signals will do.

It should also be appreciated that other embodiments of manipulating input signals suffice for the purposes of the present invention. For example, signal sources 34 and 36 may be digitized by separate analog-to digital converters. Digitized signals may be preprocessed by Application Specific Integrated Circuits ("ASIC") or commercial digital signal processing (DSP) circuits before being routed to other elements of the microprocessor system, and such routing may be along either serial or parallel information busses, as is well known in the art. For example, the ASIC chip could perform digital filtering in order to off-load computation from the microprocessor.

These signals are sent to the microcomputer system 44 where they are digitally high and low pass filtered (by standard methods known in the art) and stored in data arrays, $V_1(n)$ and $V_2(m)$. In one current embodiment, $V_1(n)$ and $V_2(m)$ are both sampled data arrays with each element of the array represented as a 16 bit signed integer. As a 16 bit signed integer, the range of values for each sample datum is +/−1.0 microamperes for an element of $V_1(n)$ and +/−75 millivolts for an element of $V_2(m)$. The resolution of $V_1(n)$ is approximately 500 picoamperes and for $V_2(m)$ is 2.5 microvolts. $V_1(n)$ represents a data passband from 2.5 to 12 Hertz, and $V_2(m)$ represents a data passband of 0.3 to 20 Hertz.

Each array in the current embodiment stores up to 4.5 seconds of sampled data. $V_1$ is sampled at 50 Hertz and $V_2$ is sampled at 100 Hertz—thus, $V_1(n)$ is a stored array of 225 samples for the full 4.5 seconds whereas $V_2(m)$ is a stored array of 450 samples. The main reason why $V_2$ is sampled at twice the rate of $V_1$ is that the shock/no-shock analysis of $V_2(m)$ requires higher sampling resolution than the cross-correlation function as described below.

Figure 7:
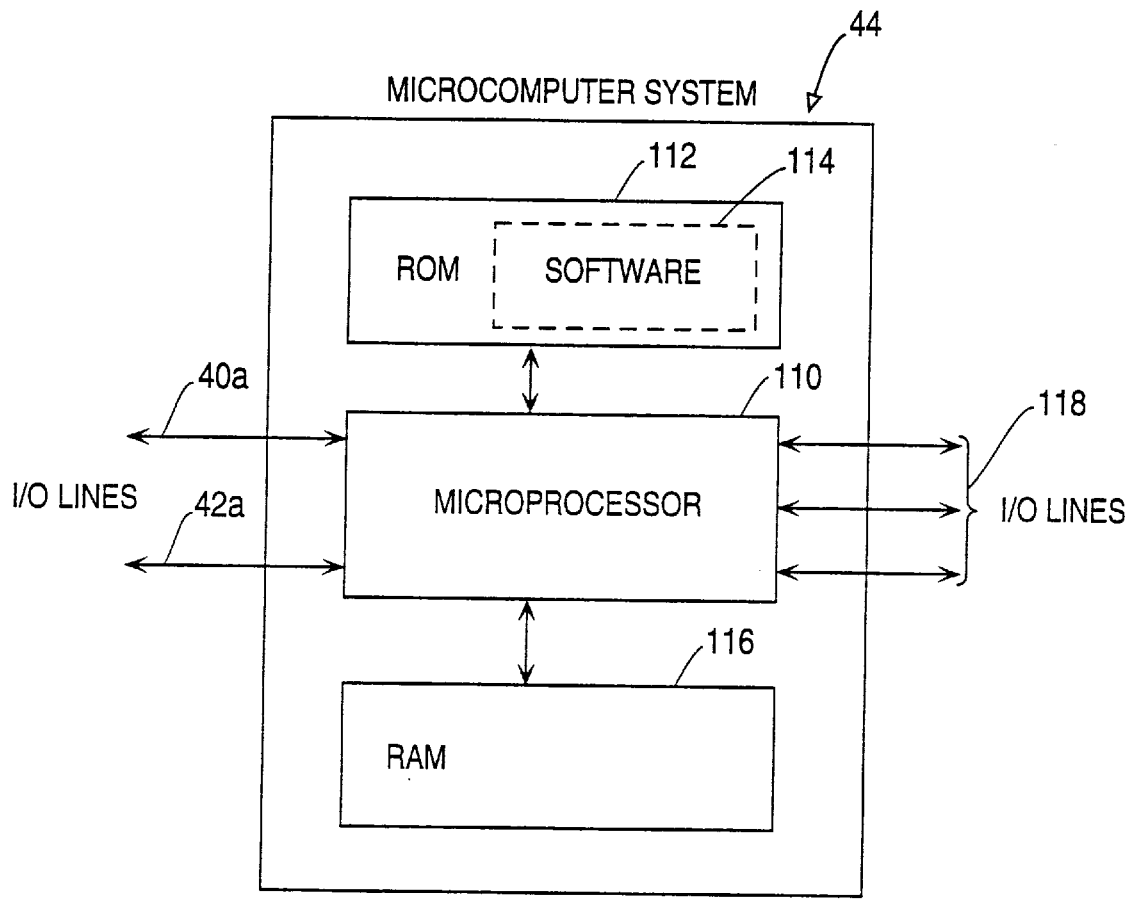
FIG. 7 is an expanded block diagram of the microprocessor system that processes intermediate signal data in the manner shown in FIG. 8.

A high level block diagram of an embodiment of microcomputer system 44 is given in FIG. 7. Microcomputer system 44 comprises I/O lines 40a and 42a, microprocessor 110, read-only memory 112 ("ROM") in which is stored the software 114 which directs the action of microprocessor 110, random access memory 116 ("RAM"), and other I/O lines 118.

The digital signals 40 and 42 are input through I/O lines 40a and 42a respectively into microprocessor 110. Microprocessor 110, acting under control of software 114, stores these digital signals 40 an 42 into RAM 116 as data arrays $V_1(n)$ and $V_2(m)$ respectively. As will be discussed below, these data arrays are analyzed and certain action are taken by microprocessor 110 in response to that analysis.

Other I/O lines 118 are provided for microcomputer system 54 to transmit orders for those actions or to interface with the user-operator. For example, in FIG. 1, it can be seen that operator controls 48 (such as a keyboard, a switch panel, or other interface means), display system 50, and audio/speaker system 52 are provided for a means of user interface. Additionally, an enable line, 53, is provided from microprocessor 44 to defibrillation system 54 to allow delivery of a life-saving shock from defibrillator system 54 to patient 12. This enable signal is generated after analysis of the input signal data indicates that, after noting that there is not an inordinate amount of signal corruption, the patient's differential mode input signal is consistent with a state of ventricular fibrillation. During administration of defibrillation therapy, switch 56 is closed by defibrillator system 54 in order to connect to the patient. During analysis of patient signals, switch 56 remains open to avoid placing unnecessary loading of input signals from the patient.

While microprocessor system 44 is generically depicted in FIG. 7, it will be appreciated that system 44 may be constructed from readily commercially available hardware components. For example, microprocessor 110 may be one of the processors of the Motorola 68HC16 family or the Intel x86 microprocessor family for the purposes of the present invention. Additionally, there must be sufficient RAM and ROM storage in order to store the digital data and control software.

It will also be appreciated that FIG. 7 is merely one embodiment of a microprocessor system that is sufficient for the purposes of the present invention. It is well known to those skilled in the art to design other systems that provide the same amount of functionality (e.g. storing control software in RAM instead of ROM and other variations). Accordingly, the present invention should not be limited to the particular embodiment disclosed herein.

Figure 8:
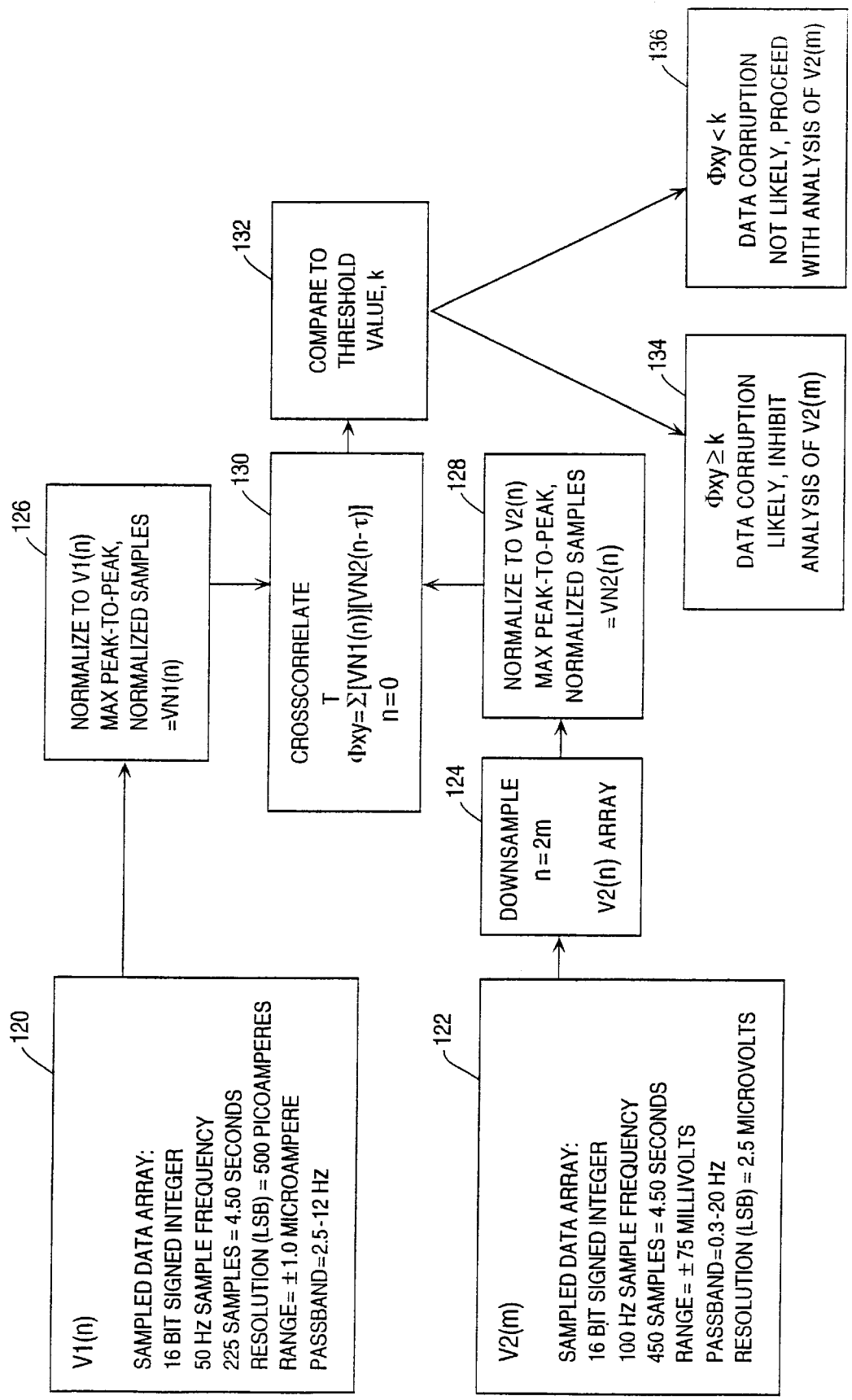
FIG. 8 is a flow chart detailing the processing of intermediate data carried out by the microprocessor system.

Now the manner of processing the digital data (i.e. sample data arrays $V_1(n)$ and $V_2(m)$) will be discussed. FIG. 8 is a flow chart depicting the processing. In block 120 and 122, the elements of the sample data arrays $V_1(n)$ and $V_2(m)$ are read out of RAM 116 in either a parallel or serial fashion, element-by-element. Each element of $V_2(m)$ is down-sampled in block 124 by half to match the sample rate of $V_1(n)$, thus producing the elements of a new array $V_2(n)$.

Each element of both $V_1(n)$ and $V_2(n)$ is then normalized in amplitude in blocks 126 and 128. This is accomplished by finding the maximum and minimum values in arrays $V_1(n)$ and $V_2(n)$ and dividing each element by the difference between the maximum and minimum values. The result is elements that are normalized in the range of −1 to +1 for both arrays. Normalization results in two new arrays—$VN_1(n)$ and $VN_2(n)$ respectively. Alternatively, normalization could be accomplished by scaling $V_1(n)$ and $V_2(n)$ such that their peak auto-correlation values are each unity, as is well known in the art.

These normalized values are then cross-correlated in block 130 as given by the following equation:

$$\phi = \sum_{n=0}^{T} [V_{N1}(n)] \cdot [V_{N2}(n-\tau)] \quad (1)$$

where T is the length of the array and $\tau$ is a time shift that maximizes $\Phi$. This time shift, $\tau$, is selected in order to adjust for any variability in the relative phase of the two input signals on which these arrays are based. $\tau$ is usually a fixed number based on predetermined signal time offsets due to filtering processes. Alternatively, $\Phi$ can be determined for iterated values of $\tau$, and the maximum value (i.e. highest correlation) is then selected.

The cross-correlation value, $\Phi$, is a quantitative measure of the similarities between the two signals 34 and 36 (i.e. $V_{icm}$ and $V_{dif}$ respectively). In fact, it can be shown that if these two signals are identical, then the cross-correlation value is maximized. It should be appreciated that the cross-correlation function given in equation 1 is only one of many possible functions known to those skilled in the art. Any other function that derives a value based upon the "goodness" of correlation between the amount of common mode signal input and the total composite signal input will suffice. Thus, the present invention should not be construed as limited to the use of the above-mentioned correlation function.

As previously mentioned, a high cross-correlation value, heuristically speaking, implies that the input signal, $V_{dif}$, is dominated by the other input signal, $V_{icm}$. In such a case, the differential mode signal is too corrupted with common mode signal to yield an accurate analysis of the state of the patient's heart. Thus, it is better, when the data becomes too corrupted, to ignore this data than to act upon it.

This heuristic is embodied in a threshold value, k, against which the cross-correlation value, $\Phi$, is compared in block 132. If $\Phi<k$, then the differential mode signal data (represented by $V_2(m)$) is not likely to be unduly corrupted by common mode signal data. In that case, the comparison is favorable and the system proceeds with the analysis of $V_2(m)$ data in block 136. If it then seems that $V_2(m)$'s data suggest that the patient's heart is in a state of fibrillation, then the microprocessing system 44 can recommend to the user that a life-saving shock be administered.

On the other hand, if $\Phi>=k$, then the differential mode signal data is likely to be too corrupted to be of any value. In such a case, microcomputer system 44 inhibits the analysis of the data in block 134 and may subsequently flush the data. Microcomputer system 44 may advise (e.g. by display or audio/visual means) the user to correct any potential situations that are known sources of common mode signal. For example, system 44 may ask the user to stop moving near the patient, stop shaking the electrode cables, and the like. System 10 will continuously monitor the data until the condition, Φ<k, is satisfied. Then, the action in block 136 can take place.

It will be appreciated that the threshold value, k, may be determined by anyone skilled in the art by conducting a series of trial and error experiments that have varying amounts of common mode and differential mode signals present. Simulated normal heart and fibrillation signal data can be fed into the system under various conditions of common mode signal presence. This and other methods of finding such heuristic values are well known to those skilled in the art.

Likewise, it should also be appreciated that several distinct values of k may be employed for the purposes of the present invention. For example, some types of heart signals, such as asystole, may be more susceptible to corruption than other, larger signals. If small amplitude ECG signals are encountered, the presently claimed device may use a modified value of k to determine if corruption is present.

In an alternative embodiment, the common mode signal data may be used independently to determine if the potential for corruption of differential mode data exists. In this embodiment, the common mode signal data 34 could itself be analyzed without direct comparison with the differential mode data channel. For example, common mode data set 104 could be analyzed by magnitude. If the magnitude of data set 104 is small, then the potential for corruption is low, and the differential mode data may be presumed to be uncorrupted. However, if the common mode data exceeds some threshold value, then the differential data is potentially corrupted, and may be discarded. This embodiment has the advantage of simplicity, but may cause differential mode data that is, in fact, not significantly corrupted to be discarded more often than the previously described embodiment.

In another alternative embodiment, the common mode signal data could in its place used to directly enhance the analysis of the differential mode signal (i.e. the ECG data signal) in order to make a decision whether to defibrillate the patient. Other embodiments, as discussed above for the present invention, have used the common mode data to determine if the differential mode data is too corrupted to accurately analyze. For example, the previous embodiments have been described as a sequential series of decisions in which it is first determined if the differential data is too corrupted to analyze, followed by an analysis of the differential data alone if the data is uncorrupted.

Thus, in this alternative embodiment, the common mode data and the differential mode data are both used concurrently to make a decision whether to defibrillate the patient. For example, both channels 34 and 36 could be used as inputs to a multivariate pattern classifier in a manner known to the art, to make a defibrillation decision.

There has thus been shown and described a novel method for the detection and use of common mode signals in instrumentation systems which meets the objects and advantages sought. As stated above, many changes, modifications, variations and other uses and applications of the subject invention will, however, become apparent to those skilled in the art after considering this specification and accompanying drawings which disclose preferred embodiments thereof. All such changes, modifications, variations and other uses and applications which do not depart from the spirit and scope of the invention are deemed to be covered by the invention which is limited only by the claims which follow.

I claim:

1. In an apparatus that detects input signals in an environment where said input signals comprise differential mode signals that potentially co-exist with common mode signals, a method for analyzing the input signal and determining whether the input signal can be used to accurately diagnose the differential mode signal; the steps of said method comprising:

(A) input a signal into the apparatus;

(B) separate the input signal into intermediate signals based on known functions of differential mode signals and common mode signals; and (C) determine whether to analyze the intermediate signal based on known function of differential mode signal data according to the amount of artifact signal present.

2. The method as recited in claim 1 wherein step (C) further comprises:

(C)(i) cross-correlate the intermediate signals to produce a correlation value; and (C)(ii) determine whether to analyze the intermediate signal based on a known function of the differential mode signal according to the correlation value produced in step (C)(i).

3. The method as recited in claim 2 wherein the steps (C)(ii) further comprises:

(C)(ii)(a) comparing the correlation value produced in step (C)(i) against a predetermined threshold value;

(C)(ii)(b) analyze the intermediate signal based on a known function of the differential mode signal if the comparison in step (C)(ii)(a) is favorable.

4. The method as recited in claim 1 wherein step (C)(ii) further comprises:

(C)(ii)(a) comparing the common mode value produced in step (C)(i) against a predetermined threshold value;

(C)(ii)(b) analyze the second intermediate signal based on a known function of the differential mode signal if the comparison in step (C)(ii)(a) is favorable.

5. The method as recited in claim 1 wherein step (B) further comprises:

separate the input into a first and a second intermediate signal wherein the first intermediate signal is a known function solely of the common mode signal and wherein the second intermediate signal is a known function of differential mode and common mode signals.

6. In an apparatus that detects input signals in an environment where said input signals comprise differential mode signals that potentially co-exist with common mode signals, a method for analyzing the input signal and determining whether the input signal can be used to accurately diagnose the differential mode signal; the steps of said method comprising:

(A) input signals into the apparatus;

(B) separate the input signals into first and second intermediate signals based on known functions of differential mode signals and common mode signals;

(C) analyze the first intermediate signal based on a known function of the common mode signal to produce a common mode signal value;

(D) determine whether to analyze the second intermediate signal based on a known function of the differential mode signal according to the common mode signal value produced in step (C).

7. An apparatus for detecting input signals in an environment where said input signals comprise differential mode signals that potentially co-exist with common mode signals, said apparatus comprising:

a means for inputting said input signals;

a means for separating said input signals into intermediate signals based on known functions of said differential mode signals and said common mode signals; and a means for determining whether to analyze an intermediate signal based on known function of differential mode signal data according to the amount of artifact signal present.

8. The apparatus as recited in claim 7 wherein said means for determining further comprises:

a means for cross-correlating the intermediate signals to produce a correlation value; and a means for determining whether to analyze the intermediate signal based on a known function of the differential mode signal according to said correlation value.

9. The apparatus as recited in claim 8 wherein said means for determining whether to analyze the intermediate signal based on a known function of the differential mode signal according to said correlation value further comprises:

a means for comparing said correlation value produced against a predetermined threshold value;

a means for analyzing said intermediate signal based on a known function of the differential mode signal if the comparison produced by said means for comparing is favorable.

10. The apparatus as recited in claim 7 wherein said means for determining further comprises:

a means for analyzing said intermediate signal based on a known function of the common mode signal to produce a common mode signal value;

a means for determining whether to analyze said intermediate signal based on a known function of the differential mode signal according to said common mode signal value.

11. The apparatus as recited in claim 10 wherein said means for determining whether to analyze said intermediate signal based on a known function of the differential mode signal according to said common mode signal value further comprises:

a means for comparing said common mode value against a predetermined threshold value;

a means for analyzing said intermediate signal based on a known function of the differential mode signal if the comparison produced by said means for comparing is favorable.

12. In a device that collects and analyzes electrocardiographic (ECG) signal information from a patient's heart, said ECG signal information being subject to corruption by other signal sources not related to the patient's heart;

a method for improving the accuracy of said analysis in the presence of corruption, the steps of said method comprising:

(A) input signal information;

(B) determine if the level of input signal information corruption inhibits an accurate analysis of the ECG portion of the input signal; and (C) if level of corruption in step (B) inhibits accurate analysis, initiate action to remove corruption from said input signal.

13. The method as recited in claim 12 wherein step (B) further comprises:

(B)(i) separate the input signal into intermediate signals based on known functions of ECG signals and other signal sources;

(B)(ii) cross-correlate the intermediate signals to produce a correlation value; and (B)(iii) determine if the level of input signal information corruption inhibits an accurate analysis of the ECG portion according to the correlation value produced in step (B)(ii).

14. The method as recited in claim 13 wherein the steps (B)(iii) further comprises:

(B)(iii)(a) comparing the correlation value produced in step (B)(ii) against a predetermined threshold value;

(B)(iii)(b) determine that the level of input signal information corruption inhibits an accurate analysis of the ECG portion if the comparison in step (B)(iii)(a) is not favorable.

15. The method as recited in claim 12 wherein step (B) further comprises:

(B)(i) separate the input signal into intermediate signals based on known functions of ECG signals and other signal sources;

(B)(ii) analyze the intermediate signal based on a known function of the other signal sources to produce an other signal source value; and (B)(iii) determine if the level of input signal information corruption inhibits an accurate analysis of the ECG portion according to the other signal source value produced in step (B)(ii).

16. The method as recited in claim 15 wherein step (B)(iii) further comprises:

(B)(iii)(a) comparing the other signal source value produced in step (B)(ii) against a predetermined threshold value;

(B)(iii)(b) determine that the level of input signal information corruption inhibits an accurate analysis of the ECG portion if the comparison in step (B)(iii)(a) is not favorable.

17. The method as recited in claim 12 wherein step (C) further comprises:

(C)(i) discard the previously input signal information and input current signal information; and (C)(ii) repeat step (B) with current signal information.

18. The method as recited in claim 12 wherein step (C) further comprises:

alerting operator to reduce the sources of potential corruption.

19. A device for collecting and analyzing electrocardiographic (ECG) signal information from a patient's heart, said ECG signal information being subject to corruption by other signal sources not related to the patient's heart; said apparatus comprising:

a means for inputting signal information;

a means for determining if the level of input signal information corruption inhibits an accurate analysis of the ECG portion of the input signal; and a means for initiating action to remove corruption from said input signal if said level of corruption determined by said means for determining inhibits accurate analysis.

20. In an ECG analyzer that detects input signals in an environment where said input signals comprise differential mode signals potentially arising from the ECG signals of a patient connected to said analyzer, said differential mode signals potentially co-existing with common mode signals, a method for analyzing the input signal and determining appropriate action based upon said analysis; the steps of said method comprising:

(A) input a signal into the apparatus;

(B) separate the input signal into intermediate signals based on known functions of differential mode signals and common mode signals; and (C) determine appropriate action according to the amount of artifact present in the input signal.

21. The method as recited in claim 20 wherein said appropriate action of step (C) further comprises:
analyze the intermediate signal based on known function of differential mode signal data.

22. The method as recited in claim 20 wherein said appropriate action of step (C) further comprises:
decide whether to defibrillate the patient based on the characteristics of the common mode signal and the characteristics of the differential mode signals present in the input signal.

23. A method for analyzing an input signal, the steps of said method comprising:
(A) collect an input signal using fewer than four electrodes separately connected to an apparatus that detects ECG signals the input signal comprising an ECG signal;
(B) determine whether artifact is present in the ECG signal, wherein step (B) comprises:
(B) determine whether converted common mode is present in the input signal.

24. A method for analyzing an input signal, the steps of said method comprising:
(A) collect an input signal comprising an ECG signal;
(B) determine whether artifact is present in the ECG signal, wherein step (B) comprises:
(B)(i) separate the input signal into first and second intermediate signals, wherein the input signal further comprises a converted common mode signal, and wherein the second intermediate signal is a known function of the ECG signal and the converted common mode signal, and
(B)(ii) compare the first and second intermediate signals to determine whether a converted common mode signal is present in the input signal.

25. A method for analyzing an input signal, the steps of said method comprising:
(A) collect an input signal comprising an ECG signal;
(B) determine whether artifact is present in the ECG signal, wherein step (B) comprises:
(B)(i) separate the input signal into first and second intermediate signals;
(B)(ii) compare the first and second intermediate signals to determine whether artifact is present in the input signal.

26. The method as recited in claim 25 wherein step (B)(ii) comprises:
(B)(ii)(a) cross-correlate the intermediate signals to produce a correlation value; and
(B)(ii)(b) use the correlation value to determine whether artifact is present in the input signal.

27. The method as recited in claim 26 wherein step (B)(ii)(b) comprises:
(B)(ii)(b) compare the correlation value against a threshold value.

28. The method as recited in claim 27 wherein the apparatus is a defibrillator, the method further comprising:
(C) determine whether to use the second intermediate signal for diagnosis of the ECG signal based on the outcome of step (B).

29. The method as recited in claim 27 wherein the apparatus is a defibrillator, the method further comprising:
(C) determine whether to use the input signal for diagnosis of the ECG signal based on the outcome of step (B).

30. An apparatus for detecting ECG artifact comprising:
means for collecting an input signal from fewer than four electrodes separately connected to the apparatus, the input signal comprising an ECG signal;
means for determining whether artifact is present in the ECG signal, wherein the means for determining comprises means for determining whether converted common mode is present in the input signal.

31. An apparatus for detecting ECG artifact comprising:
means for collecting an input signal comprising an ECG signal;
means for separating the input signal into first and second intermediate signals, and
means for comparing the first and second intermediate signals to determine whether artifact is present in the input signal.

32. The apparatus as recited in claim 31 wherein the means for separating comprises first and second operational amplifiers.

33. The apparatus as recited in claim 31 wherein the input signal further comprises a converted common mode signal, the first intermediate signal comprising a known function solely of the converted common mode signal and the second intermediate signal comprising a known function of the ECG signal and the converted common mode signal.

34. The apparatus as recited in claim 33 wherein the means for determining comprises means for cross-correlating the intermediate signals to produce a correlation value.

35. The apparatus as recited in claim 34 wherein the means for determining further comprises means for comparing the correlation value against a threshold value.

36. A method for analyzing an input signal, the steps of said method comprising:
(A) collect an input signal comprising a primary signal and artifact reference signal;
(B) compare the artifact reference signal with the input signal;
(C) if the level of artifact in the input signal is unacceptably high with respect to the input signal, alter analysis of the input signal.

37. The method of claim 36 wherein steps (B) and (C) comprise:
(B) correlating the artifact reference signal with the input signal;
(C) if the correlation between the artifact reference signal and the input signal is above a threshold, alter analysis of the input signal.

38. The method of claim 36 wherein the primary signal is an ECG signal.

39. The method of claim 36 wherein step (C) comprises:
(C) if the level of artifact in the input signal is unacceptably high with respect to the input signal, interrupt analysis of the input signal.

40. The method of claim 36 further comprising, after step (A), process the input signal to derive the artifact reference signal from the input signal as an intermediate signal.

41. A method of operating a defibrillator comprising:
(A) collect an input signal comprising an ECG signal and artifact reference signal;
(B) compare the artifact reference signal with the input signal;
(C) if the level of artifact in the input signal is unacceptably high with respect to the input signal, alter analysis of the input signal.

42. The method of claim 41 wherein step (A) comprises collecting an input signal using two electrodes.

43. The method of claim 41 wherein step (C) comprises:
(C) if the level of artifact in the input signal is unacceptably high with respect to the input signal, interrupt analysis of the input signal.

44. The method of claim 41 wherein steps (B) and (C) comprise:
(B) correlating the artifact reference signal with the input signal;
(C) if the correlation between the artifact reference signal and the input signal is above a threshold, alter analysis of the input signal.

45. The method of claim 41 further comprising, after step (A), process the input signal to derive the artifact reference signal from the input signal as an intermediate signal.

46. An apparatus for detecting artifact in an input signal comprising:
means for collecting an input signal comprising a primary signal and artifact reference signal;
means for comparing the artifact reference signal with the input signal; and
means for altering analysis of the input signal if the level of artifact is unacceptably high with respect to the input signal.

47. The apparatus of claim 46 wherein the means for comparing comprises means for correlating the primary signal and the artifact reference signal.

48. The apparatus of claim 46 wherein the primary signal is an ECG signal, the means for collecting comprising two electrodes.

* * * * *